(12) United States Patent
Lal et al.

(10) Patent No.: US 7,662,959 B2
(45) Date of Patent: Feb. 16, 2010

(54) QUATERNARY TRIFLUOROMETHYLCYCLOHEXANE DERIVATIVES FOR LIQUID CRYSTALS

(75) Inventors: Gauri Sankar Lal, Whitehall, PA (US);
Michael Ulman, Mertztown, PA (US);
David Allen Roberts, Fogelsville, PA (US); Wade Hampton Bailey, Emmaus, PA (US); William Franklin Burgoyne, Bethlehem, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/970,510

(22) Filed: Jan. 7, 2008

(65) Prior Publication Data

US 2008/0188690 A1    Aug. 7, 2008

Related U.S. Application Data

(60) Provisional application No. 60/899,679, filed on Feb. 6, 2007.

(51) Int. Cl.
*C07D 237/00*    (2006.01)

(52) U.S. Cl. ............... 544/224; 544/242; 549/369; 568/420; 570/131

(58) Field of Classification Search ............... 544/224, 544/242; 549/369; 568/420; 570/131
See application file for complete search history.

(56) References Cited

U.S. PATENT DOCUMENTS

| 6,171,665 B1 | 1/2001 | Heckmeier et al. |
| 6,551,666 B2 * | 4/2003 | Kirsch et al. ............. 428/1.1 |
| 2002/0117650 A1 | 8/2002 | Reiffenrath et al. |

OTHER PUBLICATIONS

Inoi, Takeshi. "Fluorinated Liquid Crystals." Organofluorine Chemistry: Principles and Commercial Applications. 1994 pp. 263-286. Plenum Press. New York.
Kirsch, P., Michael Heckmeir, and Kazuaki Tarumi. "Design and Synthesis of Nematic Liquid Crystals with Negative Dielectric Anisotropy." Journal of Liquid Crystals. 1999. 449-452. 26, No. 3. Taylor & Francis Ltd.

* cited by examiner

*Primary Examiner*—Deborah D Carr
(74) *Attorney, Agent, or Firm*—Lina Yang

(57) ABSTRACT

A compound having the structure: w-A-x-CY—Z($CF_3$), where CY is cyclohexane or substituted cyclohexane, exemplified by 4-trifluoromethyl-4-methylcarboxy-4'-propyl-1,1'-(bi)cyclohexane.

6 Claims, No Drawings

QUATERNARY TRIFLUOROMETHYLCYCLOHEXANE DERIVATIVES FOR LIQUID CRYSTALS

CROSS-REFERENCE TO RELATED APPLICATIONS

This application claims benefit of U.S. Provisional Application No. 60/899,679, filed Feb. 6, 2007. The disclosure of this provisional application is hereby incorporated by reference.

BACKGROUND OF THE INVENTION

Liquid crystals are an essential component of many types of optical displays. The usefulness of liquid crystals for application in this area is related to the strength and position of the polar groups in the liquid crystal molecule and the degree of dielectric anisotropy the liquid crystal exhibits (T. Inoi, Organofluorine Chemistry, Principles and Commercial Applications, Ch. 12, "Fluorinated Liquid Crystals", Plenum Press, New York, R. E. Banks et al., eds., (1994), pp. 263-286). Accordingly, the literature shows that a number of liquid crystals used in active matrix displays have evolved into those containing highly polar head groups, quite notably perfluorinated ones such as $CF_3$, (T. Inoi, ibid) which impart a dipole on the molecule in order to achieve an improved dielectric anisotropy and hence enhanced performance.

Kirsch et al in Liquid Crystals 1999, 26, 449 described the preparation of liquid crystal compositions bearing a fluorine atom and a geminal alkenyl substituent on a quaternary carbon of a cyclohexane derivative. These compounds possess negative dielectric anisotropy and formed nematic mesophases with low rotational viscosity making them suitable for use in thin film transistors with multi-domain vertical alignment. Reiffenrath and Lussem in US Published patent application SN 2002/0117650 filed 19 Jul. 2001 reported on compounds bearing a $CF_3$— group and a geminal alkynyl group on a cyclohexane derivative. They suggested that these compounds are suitable for use in liquid crystalline media.

BRIEF SUMMARY OF THE INVENTION

The present invention discloses novel compounds which can be used to synthesize liquid crystal components. The compounds of this invention possess the general structure, w-A-x-CY—Z ($CF_3$).

One embodiment of the invention includes a compound having a general structure: w-A-x-CY—Z($CF_3$);

wherein w is selected from the group consisting of: R, OR, COOR, COR, OOCR, OOCOR, O($CH_2$)$_n$OR, CH═CHCOOR, CR═CR—COOR, CN, H, I, $NH_2$, NHR, $NR_2$, SR, Br, Cl, F, $NO_2$, N═C═O, N═C═S, $CF_3$, NHCOR, $OCF_3$ and mixtures thereof; wherein R=straight or branched chain alkyl with up to 12 C atoms;

A is selected from the group consisting of: aryl, biphenyl, polyphenyl, cyclohexyl, cyclohexenyl, dioxolane, dioxane, bridged bicyclic, pyridine, pyrimidine, pyrazine, pyridazine, tetrazine and mixtures thereof;

x is selected from the group consisting of: a single bond, CH═NR, CH═CHR', N═N, COO, COS, CONH, ($CH_2$)$_n$, N═C═N, O, $CH_2$O, ($CH_2$)$_n$NH, NH, $N^+(O^-)$═N, N═CH—CH═N, COO($CH_2$)$_n$OOC, ($CH_2$)$_n$COO, ethyne, CH═$N^+(O^-)$, O($CH_2$)$_n$O and mixtures thereof; wherein R or R' is an alkyl or an aryl with up to 12 carbons; and n=1 to 5; and Z is selected from the group consisting of: COOR (wherein R=aryl, straight, branched or cycloaliphatic with or without unsaturation); lactone of 4-6 carbon atoms; COH; $CH_2OH$; CH═CRR' (wherein R or R'=alkyl or aryl with up to 12 carbons; and mixtures thereof; and CY is selected from the group consisting of cyclohexane and substituted cyclohexane.

Another embodiment of the invention includes a compound having a general structure:

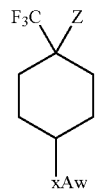

wherein w is selected from the group consisting of: R, OR, COOR, COR, OOCR, OOCOR, O($CH_2$)$_n$OR, CH═CHCOOR, CR═CR—COOR, CN, H, I, $NH_2$, NHR, $NR_2$, SR, Br, Cl, F, $NO_2$, N═C═O, N═C═S, $CF_3$, NHCOR, $OCF_3$ and mixtures thereof; wherein R=straight or branched chain alkyl with up to 12 C atoms;

A is selected from the group consisting of: aryl, biphenyl, polyphenyl, cyclohexyl, cyclohexenyl, dioxolane, dioxane, bridged bicyclic, pyridine, pyrimidine, pyrazine, pyridazine, tetrazine and mixtures thereof;

x is selected from the group consisting of: a single bond, CH═NR, CH═CHR', N═N, COO, COS, CONH, ($CH_2$)$_n$, N═C═N, O, $CH_2$O, ($CH_2$)$_n$NH, NH, $N^+(O^-)$═N, N═CH—CH═N, COO($CH_2$)$_n$OOC, ($CH_2$)$_n$COO, ethyne, CH═$N^+(O^-)$, O($CH_2$)$_n$O and mixtures thereof; wherein R or R' is an alkyl or an aryl with up to 12 carbons; and n=1 to 5; and Z is selected from the group consisting of: COOR (wherein R=aryl, straight, branched or cycloaliphatic with or without unsaturation); lactone of 4-6 carbon atoms; COH; $CH_2OH$; CH═CRR' (wherein R or R'=alkyl or aryl with up to 12 carbons); and mixtures thereof.

In the embodiments above, w is further selected from the group consisting of:

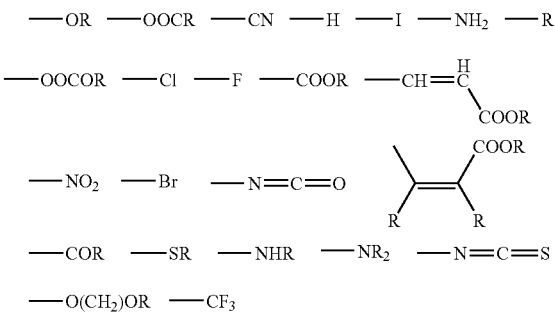

and mixtures thereof;

A is further selected from the group consisting of:

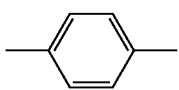 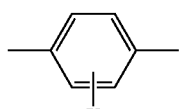

X = F, Cl, Br, I, OR,
OOCR, CH₃, CN, NO₂
R = 1-12 C

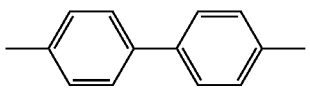 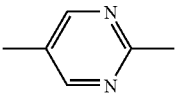

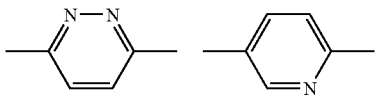

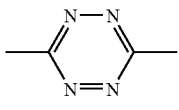

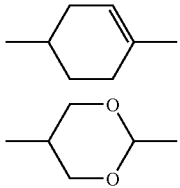

and mixtures thereof; and
x is further selected from the group consisting of:

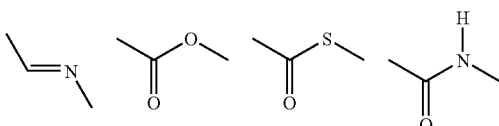

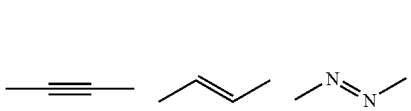

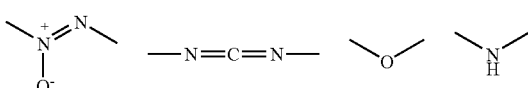

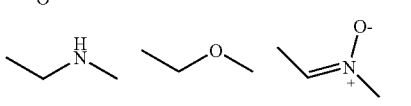

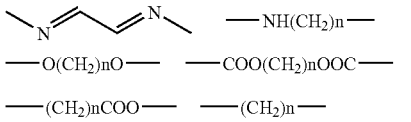

—O(CH₂)nO—   —COO(CH₂)nOOC—

—(CH₂)nCOO—   —(CH₂)n— and mixtures thereof.

Another embodiment of the invention includes a compound having a general structure: w-A-x-CY—Z(CF₃);

wherein w is selected from the group consisting of:

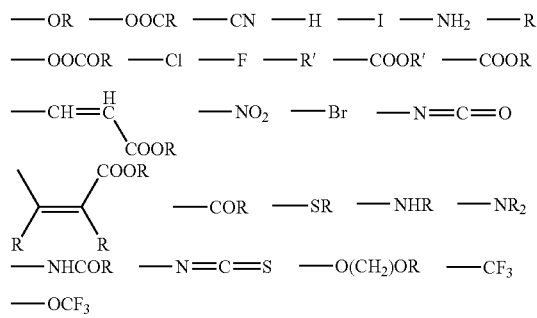

and mixtures thereof;

A is selected from the group consisting of:

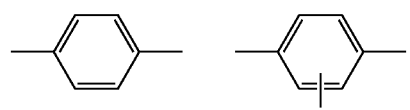

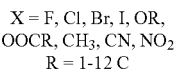

X = F, Cl, Br, I, OR,
OOCR, CH₃, CN, NO₂
R = 1-12 C

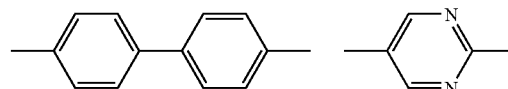 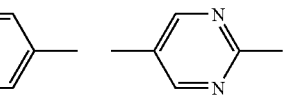

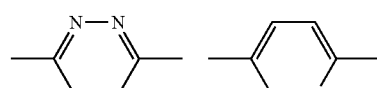

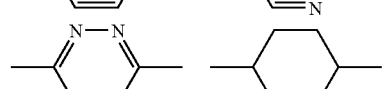

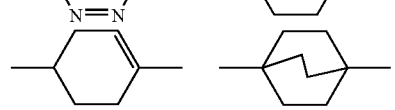

and mixtures thereof;

x is selected from the group consisting of:

-continued

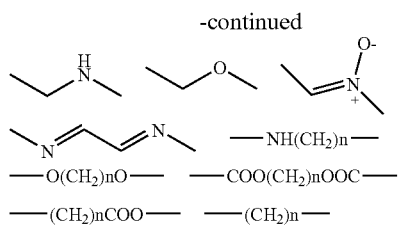

and mixtures thereof; wherein n=1 to 5;

Z is selected from the group consisting of: COOR (wherein R=aryl, straight, branched or cycloaliphatic with or without unsaturation); lactone of 4-6 carbon atoms; COH; CH$_2$OH; CH=CRR' (wherein R or R'=alkyl or aryl with up to 12 carbons); and mixtures thereof; and CY is selected from the group consisting of cyclohexane and substituted cyclohexane.

Yet, another embodiment of the invention includes a compound having a general structure:

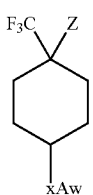

wherein;
w is selected from the group consisting of:

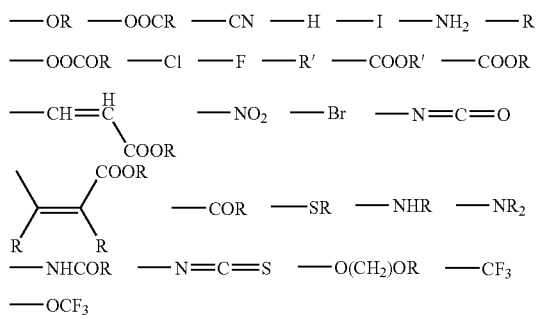

and mixtures thereof;
A is selected from the group consisting of:

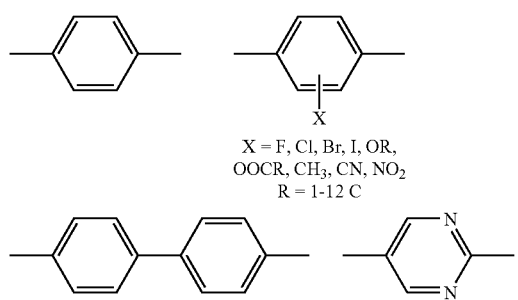

X = F, Cl, Br, I, OR, OOCR, CH$_3$, CN, NO$_2$
R = 1-12 C

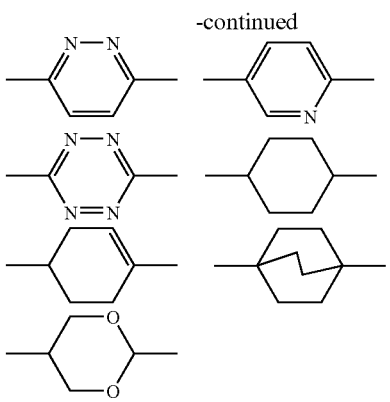

and mixtures thereof;
x is selected from the group consisting of:

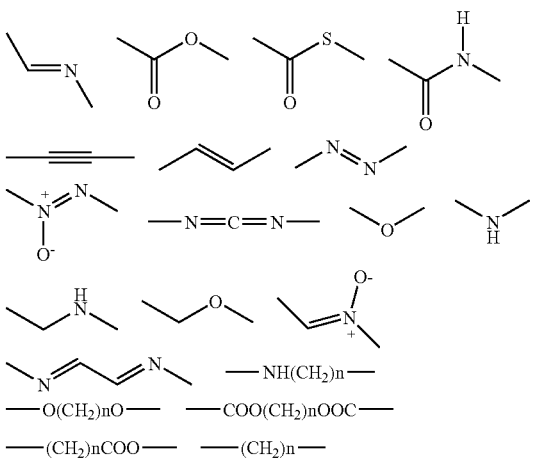

and mixtures thereof; wherein n=1 to 5; and

Z is selected from the group consisting of: COOR (wherein R=aryl, straight, branched or cycloaliphatic with or without unsaturation; lactone of 4-6 carbon atoms; COH; CH$_2$OH; CH=CRR' (wherein R or R'=alkyl or aryl with up to 12 carbons); and mixtures thereof.

Yet, another embodiment of the invention includes a compound comprising: 4-trifluoromethyl-4-methylcarboxy-4'propyl-1,1'-bi(cyclohexane).

DETAILED DESCRIPTION OF THE INVENTION

The present invention pertains to new compositions of matter, particularly, compounds bearing a cyclohexane ring with a trifluoromethyl group and a geminal substituent which may be derivatized to yield highly electrically polar molecules, particularly novel liquid crystal compositions.

This invention provides novel compositions which can be used to synthesize liquid crystal components. The compounds of this invention possess the general structure, w-A-x-CY—Z(CF$_3$), where "CY" is cyclohexane or substituted cyclohexane bearing a CF$_3$ group and a geminal substituent, Z. Formula 1 is exemplary of an embodiment of the compounds of the Present Invention;

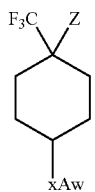

Formula 1 wherein:

"Z" is a functional entity capable of being derivatized to produce a variety of liquid crystal compositions. The Z group may include COOR, (R=straight, branched or cycloaliphatic with or without unsaturation), COOR may also be a lactone of 4-6 carbon atoms, COH, CH$_2$OH, CH=CRR' (R,R'=alkyl or aryl with up to 12 carbons);

"w" may include groups such as: R, OR, COOR, COR, OOCR, OOCOR, O(CH$_2$)$_n$OR, CH=CHCOOR, CR=CR—COOR, CN, H, I, NH$_2$, NHR, NR$_2$, SR, Br, Cl, F, NO$_2$, N=C=O, N=C=S, CF$_3$, NHCOR, OCF$_3$ where R=straight or branched chain alkyl with up to 12 C atoms, as shown in Scheme 1, below);

"A" may include aryl, biphenyl, polyphenyl, cyclohexyl, cyclohexenyl, dioxolane, dioxane, bridged bicyclic, pyridine, pyrimidine, pyrazine, pyridazine and tetrazine groups, as shown in Scheme 2, below; and "X" is a linking group between two rings and may include a single bond, CH=NR, CH=CHR', N=N, COO, COS, CONH, (CH$_2$)$_n$, N=C=N, O, CH$_2$O, (CH$_2$)$_n$NH, NH, N$^+$(O)=N,N=CH—CH=N, COO(CH$_2$)$_n$OOC—, (CH$_2$)$_n$COO, as shown in Scheme 3, below.

—OR  —OOCR  —CN  —H  —I  —NH$_2$  —R

—OOCOR  —Cl  —F  —COOR  —CH=CH-COOR (with COOR)

—NO$_2$  —Br  —N=C=O  (vinyl with R groups)

—COR  —SR  —NHR  —NR$_2$  —N=C=S

—O(CH$_2$)OR  —CF$_3$

Scheme 2: Ring systems (A) in liquid crystal compositions:

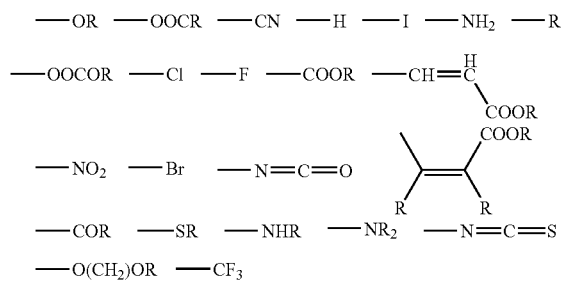

X = F, Cl, Br, I, OR, OOCR, CH$_3$, CN, NO$_2$
R = 1-12 C

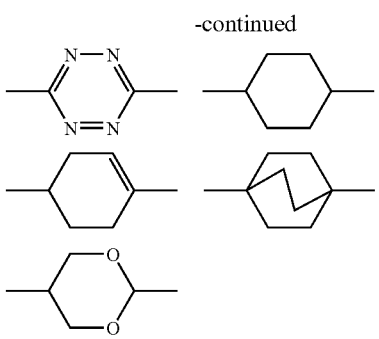

Scheme 3: Linking groups (x) in liquid crystal compositions:

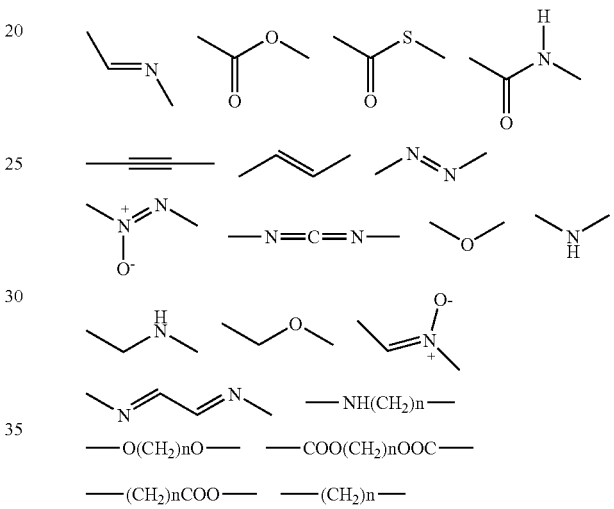

—NH(CH$_2$)n—

—O(CH$_2$)nO—    —COO(CH$_2$)nOOC—

—(CH$_2$)nCOO—    —(CH$_2$)n—

A method for preparation of compounds with Z=COOR, COH, CH$_2$OH and CH=CRR' is illustrated in Scheme 4, below. A carboxylic acid bearing group Z is reacted with SF$_4$ to obtain the CF$_3$— product which is reacted with a hydride such as LiAlH$_4$ to obtain the alcohol (Z=CH$_2$OH). Oxidation of the alcohol furnished the aldehyde (Z=COH). A Wittig reaction of the aldehyde with alkyl triphenylphosphine and base afforded the olefin (Z=CH=CRR').

Scheme 4: Synthetic method to quaternary CF$_3$:

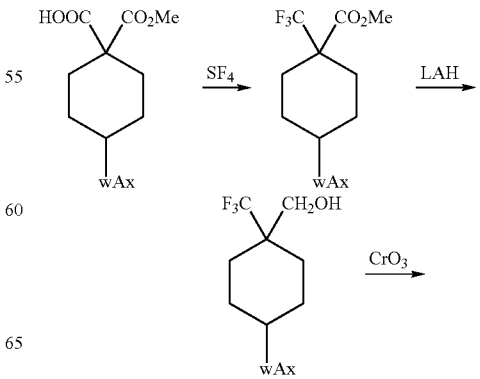

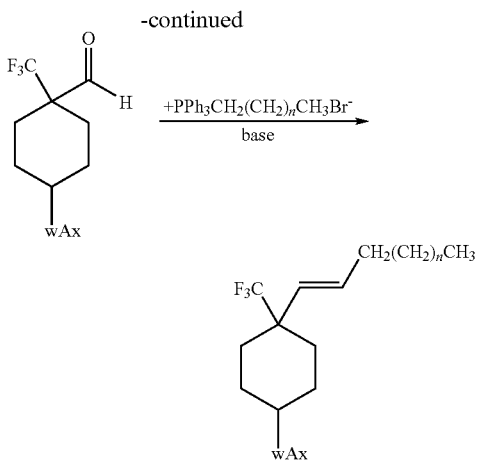

where LAH is lithium aluminum hydride.

Further transformations of the ester functionality (Z=COOR) can be carried out to prepare other esters: COOR' (R'=alkyl, aryl); amides: CONR$_2$ (R=H, alkyl or aryl); carboxylic acid: COOH; carboxylic acid chloride; alcohols: (R$_2$COH, R=alkyl or aryl); ketones: COR (R=alkyl or aryl).

Further transformation of the alcohol: Z=CH$_2$OH, can be carried out to prepare the alkyl halide: CH$_2$F, CH$_2$Cl, CH$_2$Br, CH$_2$I; ethers: CH$_2$OR (R=straight chain or branched alkyl, cycloalkyl, aryl or alkylaryl with up to 12 carbon atoms); thioethers: CH$_2$SR (R=straight chain or branched alkyl, cycloalkyl, aryl or alkylaryl with up to 10 carbon atoms); amines: CH$_2$NR$_2$ (R=H, straight chain or branched alkyl, cycloalkyl, aryl or alkylaryl with up to 12 carbon atoms); and, esters: CH$_2$OCOR (R=straight chain or branched alkyl, cycloalkyl, aryl or alkylaryl with up to 10 carbon atoms).

Further transformation of the aldehyde group (Z=COH) can be carried out to prepare olefins: CH=CR$_2$, via the Wittig or Horner-Emmons reaction (R=straight chain or branched alkyl, cycloalkyl, aryl or alkylaryl with up to 12 carbon atoms), which may be substituted with heteroatoms, such as; O, N, S or groups, such as; carboxylic ester, cyano, nitro ketone or aldehyde); alcohols: CH$_2$OH, by reduction with hydrides, such as; NaBH$_4$ or CH$_2$(OH)R (R=straight chain or branched alkyl, cycloalkyl, aryl or alkylaryl with up to 12 carbon atoms, which may substituted with heteroatoms, such as; O, N, S or groups, such as; ester, cyano, nitro ketone or aldehyde), by reaction with organometallic reagents, such as; R$^-$M$^+$ (M=Li, Na, K), RMgX (X=, Br, Cl), R$_2$CuLi or R$_2$Zn, dioxolane: CHO(CH$_2$)$_n$O (n=2 or 3) by acid catalyzed condensation with 1,3-propanediol or 1,2-ethanediol, dithiolane: CHS(CH$_2$)$_n$S (n=2 or 3) by acid catalyzed condensation with 1,3-propanethiol or ethanedithiol.

Further transformation of the olefin (Z=CH=CRR') can be carried out to obtain other olefins: CH=CR$_2$R$_3$ (R$_2$, R$_3$=alkyl chains of up to 12 carbon atoms) by methathesis reactions catalyzed by tungsten, molybdenum, ruthenium or rhenium complexes. Addition of halogens will produce: CHXCRR'X (X=F, Cl, Br, I); and hydrogen halide will produce: CH$_2$CXRR'. (X=F, Cl, Br, I). Hydroboration and oxidation of the olefin will produce alcohols: CH(OH)CHRR'. Epoxidation with peracids or peroxides will generate the corresponding epoxide: CH(O)CRR' (R, R'=individually alkyl or aryl with up to 12 carbons).

The following examples are provided for the purpose of further illustrating the present invention but are by no means intended to limit the same.

Example 1

Fluorination of 4-carboxy-4-methylcarboxy-(4'propylcyclohexyl)cyclohexane with sulfur tetrafluoride 4.2 grams of 4-carboxy-4-methylcarboxy-(4'propylcyclohexyl)cyclohexane were placed in a 75 mL Hoke cylinder fitted with tee connected to a relief device and an inlet valve and containing a magnetic stir bar. The Hoke cylinder was evacuated and cooled to −78° C. 9.4 g of hydrogen fluoride was vacuum transferred into the cooled cylinder along with 9.5 molar equivalents of sulfur tetrafluoride. The valve on the cylinder was closed and it was allowed to warm up to room temperature. The reaction was allowed to stir at room temperature for 24 hours. The volatiles were evacuated from the Hoke cylinder and the residual contents were extracted with diethyl ether and neutralized over sodium bicarbonate. The mixture was filtered, concentrated and passed through a plug of silica gel, eluting with 2-4% ethyl acetate in hexanes (vol/vol). A GC-MS chromatogram showed four product peaks, corresponding to the four axial/equatorial isomers, each with a molecular ion peak (m/z=334). Upon solvent evaporation, the reaction yielded 2.0 grams of product.

Example 2

Reduction of 4-trifluoromethyl-4-methylcarboxy-(4'propylcyclohexyl)cyclohexane with lithium aluminum hydride 200 milligrams of lithium aluminum hydride was placed in a dry two neck 100 mL round bottom flask under nitrogen. 10 mL anhydrous tetrahydrofuran was added and the flask was cooled to 0° C. in an ice bath. 1.45 grams of 4-trifluoromethyl-4-methylcarboxy-(4'propylcyclohexyl)cyclohexane was dissolved in 6 mL anhydrous tetrahydrofuran and added dropwise to the reaction flask. The reaction was stirred for 1 hour at 0° C. and then 4 hours at room temperature. The reaction mixture was diluted with diethyl ether and 0.25 mL water was slowly added, followed by 0.25 mL 15% NaOH (aq), followed by 0.75 mL water. The mixture was stirred overnight. After filtration of the aluminum salts, the organic phase was washed twice with water, dried over magnesium sulfate, filtered and concentrated to yield 1.0 gram of product. A GC-MS chromatogram showed three distinct peaks (presumably the fourth was hidden under one of the other three) for the axial/equatorial isomers, each having a molecular ion peak (m/z=306).

Example 3

Oxidation of 4-trifluoromethyl-4-hydroxymethyl-(4'propylcyclohexyl)cyclohexane with chromic anhydride/pyridine 1.0 g of chromic anhydride was placed in a dry two neck round bottom flask under nitrogen. 10 mL anhydrous methylene chloride was added followed by 1.7 mL anhydrous pyridine. The mixture was allowed to stir for 40 minutes at room temperature. 1.0 g 4-trifluoromethyl-4-hydroxymethyl-(4'propylcyclohexyl)cyclohexane was added in 6 mL anhydrous methylene chloride and allowed to stir over a weekend. The reaction was diluted with ether and the precipitate was filtered through celite. The organic phase was washed twice with dilute HCl solution, once with NaHCO₃ solution and once with water, followed by drying over magnesium sulfate and evaporation of the solvents yielded 0.59 grams of material. A GC-MS chromatogram showed peaks with a molecular ion peak (m/z=302).

Example 4

Wittig reaction of the 4-trifluoromethyl-4-formyl-(4'propylcyclohexyl)cyclohexane 6.25 grams of hexyl phosphonium bromide was placed in a two neck dry round bottom flask under nitrogen. 30 mL anhydrous tetrahydrofuran was added and cooled to −70° C. 5.8 mL 2.5M n-butyl lithium in hexanes was added dropwise with stirring and all the salts dissolved to form an orange solution. The cooling bath was lowered slightly and 4.04 grams 4-trifluoromethyl-4-formyl-(4'propylcyclohexyl)cyclohexane in 10 mL tetrahydrofuran was added slowing and allowed to stir two hours. Diethyl ether was added, and the reaction mixture was washed with dilute HCl (aq) and subsequently with saturated sodium bicarbonate solution. The organic phase was concentrated and triturated with hexanes. The hexanes were passed through a plug of silica, which was subsequently washed with additional hexanes. The combined hexanes solvent was evaporated to yield 4.21 g of product. A GC-MS chromatogram showed a molecular ion peak (m/z=372).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

The invention claimed is:

1. A compound having the structure:

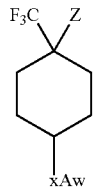

wherein;
w is selected from the group consisting of: R, OR, COOR, COR, OOCR, OOCOR, O(CH₂)ₙOR, CH=CHCOOR, CR=CR—COOR, CN, H, I, NH₂, NHR, NR₂, SR, Br, Cl, F, NO₂, N=C=O, N=C=S, CF₃, NHCOR, OCF₃ and mixtures thereof; wherein R is straight or branched chain alkyl with up to 12 C atoms;
A is selected from the group consisting of: aryl, biphenyl, polyphenyl, cyclohexyl, cyclohexenyl, dioxolane, dioxane, bridged bicyclic, pyridine, pyrimidine, pyrazine, pyridazine, tetrazine and mixtures thereof;
x is selected from the group consisting of: a single bond, CH=NR, CH=CHR', N=N, COO, COS, CONH, (CH₂)ₙ, N=C=N, O, CH₂O, (CH₂)ₙNH, NH, N⁺(O⁻)=, N,N=CH—CH=N, COO(CH₂)ₙOOC, (CH₂)ₙ COO, ethyne, CH=N⁺(O⁻), O(CH₂)ₙO and mixtures thereof; wherein R or R' is an alkyl or an aryl with up to 12 carbons; and n=1 to 5; and,
Z is selected from the group consisting of: COOR (wherein R=aryl, straight, branched or cycloaliphatic with or without unsaturation); lactone of 4-6 carbon atoms; COH; CH₂OH; CH=CRR'; (wherein R or R' is an alkyl or an aryl with up to 12 carbons); and mixtures thereof.

2. The compound of claim 1 wherein w is selected from the group consisting of:

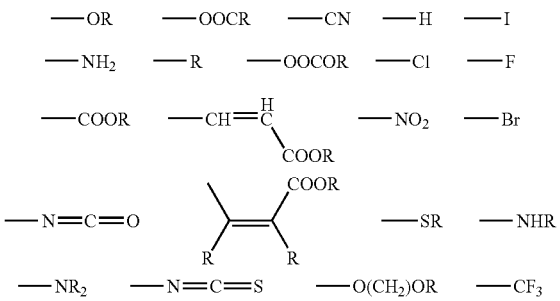

and mixtures thereof.

3. The compound of claim 1 wherein A is selected from the group consisting of:

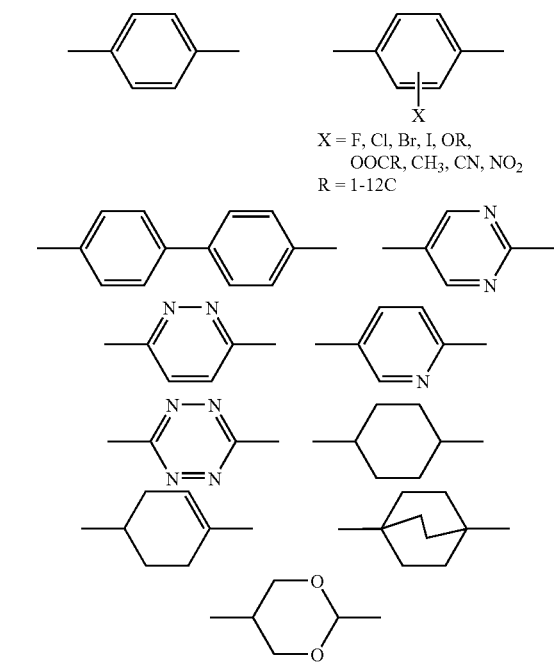

and mixtures thereof.

4. The compound of claim 1 wherein x is selected from the group consisting of:

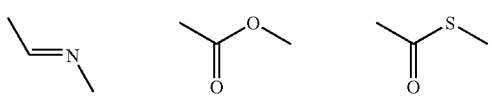

-continued

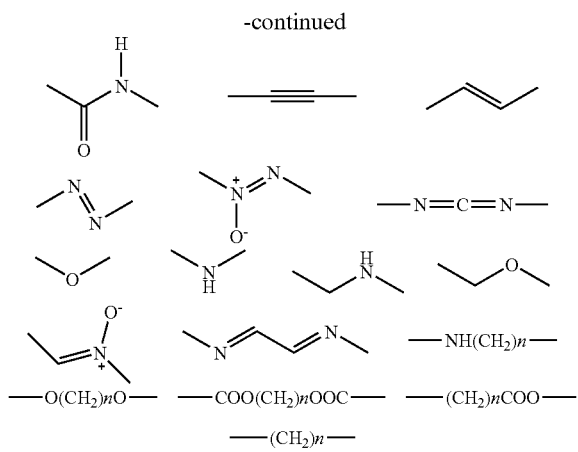

and mixtures thereof.

5. A compound having the structure:

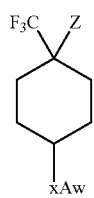

wherein;
w is selected from the group consisting of:

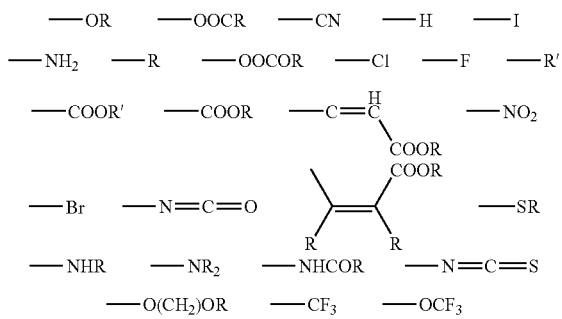

and mixtures thereof;
A is selected from the group consisting of:

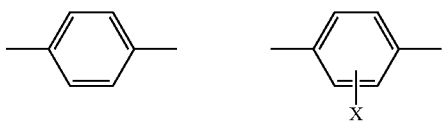

X = F, Cl, Br, I, OR, OOCR, CH₃, CN, NO₂
R = 1-12C

-continued

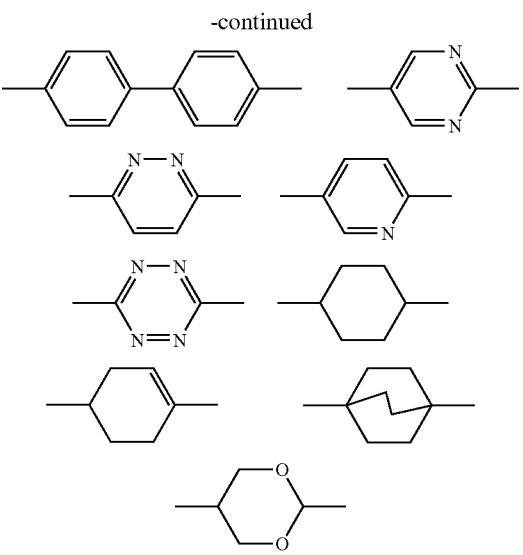

and mixtures thereof;
x is selected from the group consisting of:

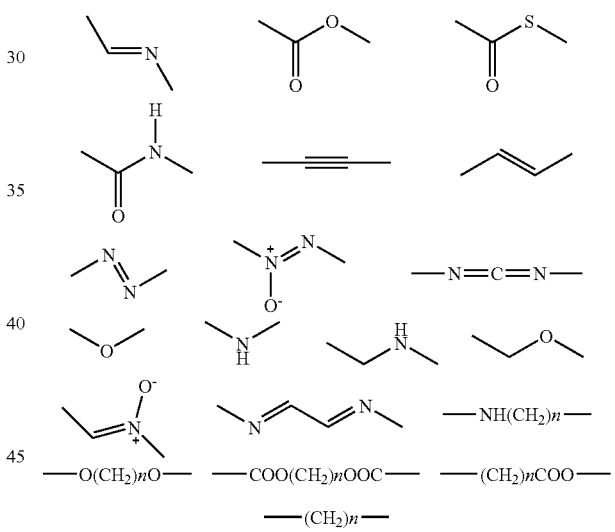

and mixtures thereof; wherein n=1 to 5; and,

Z is selected from the group consisting of: COOR (wherein R=aryl, straight, branched or cycloaliphatic with or without unsaturation); lactone of 4-6 carbon atoms; COH; CH₂OH; CH=CRR' (wherein R or R' is an alkyl or an aryl with up to 12 carbons); and mixtures thereof.

6. A compound comprising: 4-trifluoromethyl-4-methyl-carboxy-4'-propyl-1,1'(bi)cyclohexane.

* * * * *